United States Patent
Zammataro

(10) Patent No.: US 9,642,627 B2
(45) Date of Patent: May 9, 2017

(54) SELF-CENTERING CLIP AND JAW

(71) Applicant: Covidien LP, Mansfield, MA (US)

(72) Inventor: Tom Zammataro, Hamden, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/665,623

(22) Filed: Mar. 23, 2015

(65) Prior Publication Data
US 2015/0190139 A1     Jul. 9, 2015

Related U.S. Application Data

(62) Division of application No. 13/196,109, filed on Aug. 2, 2011, now Pat. No. 9,011,464.
(Continued)

(51) Int. Cl.
*A61B 17/10*     (2006.01)
*A61B 17/128*    (2006.01)
(Continued)

(52) U.S. Cl.
CPC ........ *A61B 17/1285* (2013.01); *A61B 17/122* (2013.01); *A61B 17/128* (2013.01);
(Continued)

(58) Field of Classification Search
CPC . A61B 17/1285; A61B 17/122; A61B 17/128; A61B 17/12; A61B 2017/12004; A61B 2017/0488
(Continued)

(56) References Cited

U.S. PATENT DOCUMENTS 3,120,230 A     2/1964 Skold
3,270,745 A *   9/1966 Wood ............................ 606/158
(Continued)

FOREIGN PATENT DOCUMENTS

AU     2010200641 A1   10/2010
CN        1994236 A     7/2007
(Continued)

OTHER PUBLICATIONS

The extended European Search Report corresponding to European Application No. EP 07 25 3905.9, completed Jan. 29, 2008; mailed Feb. 7, 2008; (7 Pages).
(Continued)

*Primary Examiner* — Jing Ou

(57) ABSTRACT

An apparatus for applying surgical clips to tissue includes a handle assembly having a trigger and a shaft extending therefrom. The shaft includes at least one surgical clip therein. Each clip includes a pair of legs connected by a crossbar. Each of the pair of legs has an inwardly and an outwardly facing surface, the outwardly facing surface having a raised profile protruding therefrom and extending longitudinally therealong. A jaw assembly is disposed at a distal end of the shaft and includes first and second opposed jaws moveable between a spaced apart and an approximated position. Each jaw defines a recess extending longitudinally along opposing inner surfaces thereof. Each recess defines a longitudinally extending groove having a profile substantially complementary to the raised profile of the legs of the clips. The legs of each clip are positionable at least partially within respective grooves of the recesses of the jaws.

18 Claims, 6 Drawing Sheets

Related U.S. Application Data

(60) Provisional application No. 61/409,131, filed on Nov. 2, 2010.

(51) Int. Cl.
*A61B 17/122* (2006.01)
*A61B 17/12* (2006.01)
*A61B 17/04* (2006.01)

(52) U.S. Cl.
CPC .............. *A61B 17/10* (2013.01); *A61B 17/12* (2013.01); *A61B 2017/0488* (2013.01); *A61B 2017/12004* (2013.01)

(58) Field of Classification Search
USPC .................. 606/139, 142, 143, 157, 158
See application file for complete search history.

(56) References Cited

U.S. PATENT DOCUMENTS

| | | | |
|---|---|---|---|
| 3,363,628 | A | 1/1968 | Wood |
| 3,631,707 | A | 1/1972 | Miller |
| 3,638,847 | A | 2/1972 | Noiles et al. |
| 3,735,762 | A | 5/1973 | Bryan et al. |
| 3,867,944 | A | 2/1975 | Samuels |
| 4,242,902 | A | 1/1981 | Green |
| 4,296,751 | A | 10/1981 | Blake, III et al. |
| 4,372,316 | A | 2/1983 | Blake, III et al. |
| 4,408,603 | A | 10/1983 | Blake, III et al. |
| 4,412,539 | A | 11/1983 | Jarvik |
| 4,478,220 | A | 10/1984 | Di Giovanni et al. |
| 4,480,640 | A | 11/1984 | Becht |
| 4,480,641 | A | 11/1984 | Failla et al. |
| 4,487,204 | A | 12/1984 | Hrouda |
| 4,487,205 | A | 12/1984 | Di Giovanni et al. |
| 4,491,133 | A | 1/1985 | Menges et al. |
| 4,492,232 | A | 1/1985 | Green |
| 4,498,476 | A | 2/1985 | Cerwin et al. |
| 4,500,024 | A | 2/1985 | DiGiovanni et al. |
| 4,509,518 | A | 4/1985 | McGarry et al. |
| 4,512,345 | A | 4/1985 | Green |
| 4,522,207 | A | 6/1985 | Klieman et al. |
| 4,527,562 | A * | 7/1985 | Mericle ............ 606/158 |
| 4,532,925 | A | 8/1985 | Blake, III |
| 4,534,351 | A | 8/1985 | Rothfuss et al. |
| 4,545,377 | A | 10/1985 | Cerwin et al. |
| 4,549,544 | A | 10/1985 | Favaron |
| 4,550,729 | A * | 11/1985 | Cerwin et al. ........ 606/158 |
| 4,556,058 | A | 12/1985 | Green |
| 4,557,263 | A | 12/1985 | Green |
| 4,562,839 | A | 1/1986 | Blake, III et al. |
| 4,572,183 | A | 2/1986 | Juska |
| 4,576,165 | A | 3/1986 | Green et al. |
| 4,576,166 | A | 3/1986 | Montgomery et al. |
| 4,579,118 | A * | 4/1986 | Failla .............. 606/158 |
| 4,590,937 | A | 5/1986 | Deniega |
| 4,598,711 | A | 7/1986 | Deniega |
| 4,602,631 | A | 7/1986 | Funatsu |
| 4,611,595 | A | 9/1986 | Klieman et al. |
| 4,612,932 | A | 9/1986 | Caspar et al. |
| 4,616,650 | A | 10/1986 | Green et al. |
| 4,616,651 | A | 10/1986 | Golden |
| 4,624,254 | A | 11/1986 | McGarry et al. |
| 4,637,395 | A | 1/1987 | Caspar et al. |
| 4,638,804 | A * | 1/1987 | Jewusiak .............. 606/158 |
| 4,646,740 | A | 3/1987 | Peters et al. |
| 4,647,504 | A | 3/1987 | Kimimura et al. |
| 4,658,822 | A | 4/1987 | Kees, Jr. |
| 4,660,558 | A | 4/1987 | Kees, Jr. |
| 4,662,373 | A | 5/1987 | Montgomery et al. |
| 4,662,374 | A | 5/1987 | Blake, III |
| 4,671,278 | A | 6/1987 | Chin |
| 4,671,282 | A | 6/1987 | Tretbar |
| 4,674,504 | A | 6/1987 | Klieman et al. |
| 4,681,107 | A | 7/1987 | Kees, Jr. |
| 4,696,396 | A | 9/1987 | Samuels |
| 4,702,247 | A | 10/1987 | Blake, III et al. |
| 4,706,668 | A | 11/1987 | Backer |
| 4,712,549 | A | 12/1987 | Peters et al. |
| 4,733,666 | A | 3/1988 | Mercer, Jr. |
| 4,759,364 | A | 7/1988 | Boebel |
| 4,765,335 | A | 8/1988 | Schmidt et al. |
| 4,777,949 | A | 10/1988 | Perlin |
| 4,796,625 | A | 1/1989 | Kees, Jr. |
| 4,799,481 | A | 1/1989 | Transue et al. |
| 4,815,466 | A | 3/1989 | Perlin |
| 4,821,721 | A | 4/1989 | Chin et al. |
| 4,822,348 | A | 4/1989 | Casey |
| 4,834,096 | A | 5/1989 | Oh et al. |
| 4,850,355 | A | 7/1989 | Brooks et al. |
| 4,854,317 | A | 8/1989 | Braun |
| 4,856,517 | A | 8/1989 | Collins et al. |
| 4,929,239 | A | 5/1990 | Braun |
| 4,931,058 | A | 6/1990 | Cooper |
| 4,934,364 | A | 6/1990 | Green |
| 4,957,500 | A | 9/1990 | Liang et al. |
| 4,966,603 | A | 10/1990 | Focelle et al. |
| 4,967,949 | A | 11/1990 | Sandhaus |
| 4,979,950 | A * | 12/1990 | Transue et al. ............ 606/158 |
| 4,983,176 | A | 1/1991 | Cushman et al. |
| 4,988,355 | A | 1/1991 | Leveen et al. |
| 5,002,552 | A | 3/1991 | Casey |
| 5,026,379 | A | 6/1991 | Yoon |
| 5,030,224 | A | 7/1991 | Wright et al. |
| 5,030,226 | A | 7/1991 | Green et al. |
| 5,032,127 | A | 7/1991 | Frazee et al. |
| 5,035,692 | A | 7/1991 | Lyon et al. |
| 5,047,038 | A | 9/1991 | Peters et al. |
| 5,049,152 | A | 9/1991 | Simon et al. |
| 5,049,153 | A | 9/1991 | Nakao et al. |
| 5,053,045 | A | 10/1991 | Schmidt et al. |
| 5,059,202 | A | 10/1991 | Liang et al. |
| 5,062,846 | A | 11/1991 | Oh et al. |
| 5,078,731 | A | 1/1992 | Hayhurst |
| 5,084,057 | A | 1/1992 | Green et al. |
| 5,100,416 | A | 3/1992 | Oh et al. |
| 5,100,420 | A | 3/1992 | Green et al. |
| 5,104,394 | A | 4/1992 | Knoepfler |
| 5,104,395 | A | 4/1992 | Thornton et al. |
| 5,112,343 | A | 5/1992 | Thornton |
| 5,122,150 | A | 6/1992 | Puig |
| 5,127,915 | A | 7/1992 | Mattson |
| 5,129,885 | A | 7/1992 | Green et al. |
| 5,156,608 | A | 10/1992 | Troidl et al. |
| 5,160,339 | A | 11/1992 | Chen et al. |
| 5,163,945 | A | 11/1992 | Ortiz et al. |
| 5,171,247 | A | 12/1992 | Hughett et al. |
| 5,171,249 | A | 12/1992 | Stefanchik et al. |
| 5,171,250 | A | 12/1992 | Yoon |
| 5,171,251 | A | 12/1992 | Bregen et al. |
| 5,171,252 | A | 12/1992 | Friedland |
| 5,171,253 | A | 12/1992 | Klieman |
| 5,192,288 | A | 3/1993 | Thompson et al. |
| 5,197,970 | A | 3/1993 | Green et al. |
| 5,199,566 | A | 4/1993 | Ortiz et al. |
| 5,201,746 | A | 4/1993 | Shichman |
| 5,201,900 | A | 4/1993 | Nardella |
| 5,207,691 | A | 5/1993 | Nardella |
| 5,207,692 | A | 5/1993 | Kraus et al. |
| 5,217,473 | A | 6/1993 | Yoon |
| 5,219,353 | A | 6/1993 | Garvey, III et al. |
| 5,246,450 | A | 9/1993 | Thornton et al. |
| 5,269,792 | A | 12/1993 | Kovac et al. |
| 5,281,228 | A | 1/1994 | Wolfson |
| 5,282,807 | A | 2/1994 | Knoepfler |
| 5,282,808 | A | 2/1994 | Kovac et al. |
| 5,282,832 | A | 2/1994 | Toso et al. |
| 5,289,963 | A | 3/1994 | McGarry et al. |
| 5,290,299 | A | 3/1994 | Fain et al. |
| 5,300,081 | A | 4/1994 | Young et al. |
| 5,304,183 | A | 4/1994 | Gourlay et al. |
| 5,306,280 | A | 4/1994 | Bregen et al. |
| 5,306,283 | A | 4/1994 | Conners |
| 5,312,426 | A | 5/1994 | Segawa et al. |

(56) References Cited

U.S. PATENT DOCUMENTS

| | | |
|---|---|---|
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,356,064 A | 10/1994 | Green et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,913,862 A | 6/1999 | Ramsey et al. |
| 5,918,791 A | 7/1999 | Sorrentino et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |

(56) References Cited

U.S. PATENT DOCUMENTS

| | | |
|---|---|---|
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,743,240 B2 | 6/2004 | Smith et al. |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,863,675 B2 * | 3/2005 | Wilson, Jr. ................... 606/157 |
| 6,869,435 B2 | 3/2005 | Blake, III |
| 6,869,436 B2 | 3/2005 | Wendlandt |
| 6,889,116 B2 | 5/2005 | Jinno |
| 6,896,682 B1 | 5/2005 | McClellan et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,052,504 B2 | 5/2006 | Hughett |
| 7,056,330 B2 | 6/2006 | Gayton |
| 7,108,703 B2 | 9/2006 | Danitz et al. |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,232,445 B2 | 6/2007 | Kortenbach et al. |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,316,693 B2 | 1/2008 | Viola |
| 7,316,696 B2 | 1/2008 | Wilson, Jr. et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,510,562 B2 | 3/2009 | Lindsay |
| 7,552,853 B2 | 6/2009 | Mas et al. |
| 7,637,917 B2 | 12/2009 | Whitfield et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,248 B2 | 6/2010 | Smith et al. |
| 7,731,724 B2 | 6/2010 | Huitema et al. |
| 7,740,641 B2 | 6/2010 | Huitema |
| 7,752,853 B2 | 7/2010 | Singh et al. |
| 7,753,250 B2 | 7/2010 | Clauson et al. |
| 7,819,886 B2 | 10/2010 | Whitfield et al. |
| 7,887,553 B2 | 2/2011 | Lehman et al. |
| 7,905,890 B2 | 3/2011 | Whitfield et al. |
| 7,942,885 B2 | 5/2011 | Sixto, Jr. et al. |
| 7,963,433 B2 | 6/2011 | Whitman et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,056,565 B2 | 11/2011 | Zergiebel |
| 8,062,310 B2 | 11/2011 | Shibata et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |

(56) References Cited

U.S. PATENT DOCUMENTS

| | | |
|---|---|---|
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,142,451 B2 | 3/2012 | Boulnois et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,187,290 B2 | 5/2012 | Buckman et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,282,655 B2 | 10/2012 | Whitfield et al. |
| 8,308,743 B2 | 11/2012 | Matsuno et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,945 B2 | 3/2013 | Whitfield et al. |
| 8,403,946 B2 | 3/2013 | Whitfield et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,717 B2 | 11/2013 | Sorrentino et al. |
| 8,603,109 B2 | 12/2013 | Aranyi et al. |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,709,027 B2 | 4/2014 | Adams et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,821,516 B2 | 9/2014 | Huitema |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,920,438 B2 | 12/2014 | Aranyi et al. |
| 8,961,542 B2 | 2/2015 | Whitfield et al. |
| 8,968,337 B2 | 3/2015 | Whitfield et al. |
| 8,973,804 B2 | 3/2015 | Hess et al. |
| 9,011,464 B2 | 4/2015 | Zammataro |
| 9,011,465 B2 | 4/2015 | Whitfield et al. |
| 2001/0047178 A1 | 11/2001 | Peters |
| 2002/0040226 A1 | 4/2002 | Laufer et al. |
| 2002/0068947 A1 | 6/2002 | Kuhns et al. |
| 2002/0082618 A1 | 6/2002 | Shipp et al. |
| 2002/0087169 A1 | 7/2002 | Brock et al. |
| 2002/0087170 A1 | 7/2002 | Kuhns et al. |
| 2002/0099388 A1 | 7/2002 | Mayenberger |
| 2002/0120279 A1 | 8/2002 | Deguillebon et al. |
| 2002/0128668 A1 | 9/2002 | Manetakis et al. |
| 2002/0177859 A1 | 11/2002 | Monassevitch et al. |
| 2002/0198537 A1 | 12/2002 | Smith et al. |
| 2002/0198538 A1 | 12/2002 | Kortenbach et al. |
| 2002/0198539 A1 | 12/2002 | Sixto et al. |
| 2002/0198540 A1 | 12/2002 | Smith et al. |
| 2002/0198541 A1 | 12/2002 | Smith et al. |
| 2003/0014060 A1 | 1/2003 | Wilson et al. |
| 2003/0018345 A1 | 1/2003 | Green |
| 2003/0023249 A1 | 1/2003 | Manetakis |
| 2003/0040759 A1 | 2/2003 | de Guillebon et al. |
| 2003/0105476 A1 | 6/2003 | Sancoff et al. |
| 2003/0114867 A1 | 6/2003 | Bolduc et al. |
| 2003/0135224 A1 | 7/2003 | Blake |
| 2003/0167063 A1 | 9/2003 | Kerr |
| 2003/0208231 A1 | 11/2003 | Williamson et al. |
| 2003/0220657 A1 | 11/2003 | Adams |
| 2003/0225423 A1 | 12/2003 | Huitema |
| 2003/0229360 A1 | 12/2003 | Gayton |
| 2003/0233105 A1 | 12/2003 | Gayton |
| 2004/0010272 A1 | 1/2004 | Manetakis et al. |
| 2004/0044352 A1 | 3/2004 | Fowler et al. |
| 2004/0097970 A1 | 5/2004 | Hughett |
| 2004/0097971 A1 | 5/2004 | Hughett |
| 2004/0097972 A1 | 5/2004 | Shipp et al. |
| 2004/0106936 A1 | 6/2004 | Shipp et al. |
| 2004/0133215 A1 | 7/2004 | Baxter |
| 2004/0138681 A1 | 7/2004 | Pier |
| 2004/0153100 A1 | 8/2004 | Ahlberg et al. |
| 2004/0158266 A1 | 8/2004 | Damarati |
| 2004/0162567 A9 | 8/2004 | Adams |
| 2004/0167545 A1 | 8/2004 | Sadler et al. |
| 2004/0176776 A1 | 9/2004 | Zubok et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2005/0080440 A1 | 4/2005 | Durgin et al. |
| 2005/0090837 A1 | 4/2005 | Sixto et al. |
| 2005/0090838 A1 | 4/2005 | Sixto et al. |
| 2005/0096670 A1 | 5/2005 | Wellman et al. |
| 2005/0096671 A1 | 5/2005 | Wellman et al. |
| 2005/0096672 A1 | 5/2005 | Manetakis et al. |
| 2005/0101975 A1 | 5/2005 | Nguyen et al. |
| 2005/0107807 A1 | 5/2005 | Nakao |
| 2005/0107809 A1 | 5/2005 | Litscher et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0113847 A1 | 5/2005 | Gadberry et al. |
| 2005/0119671 A1 | 6/2005 | Reydel et al. |
| 2005/0119673 A1 | 6/2005 | Gordon et al. |
| 2005/0119677 A1 | 6/2005 | Shipp |
| 2005/0125010 A1 | 6/2005 | Smith et al. |
| 2005/0143767 A1 | 6/2005 | Kimura et al. |
| 2005/0149063 A1 | 7/2005 | Young et al. |
| 2005/0149064 A1 | 7/2005 | Peterson et al. |
| 2005/0149068 A1 | 7/2005 | Williams et al. |
| 2005/0149069 A1 | 7/2005 | Bertolero et al. |
| 2005/0165415 A1 | 7/2005 | Wales |
| 2005/0165418 A1 | 7/2005 | Chan |
| 2005/0171560 A1 | 8/2005 | Hughett |
| 2005/0175703 A1 | 8/2005 | Hunter et al. |
| 2005/0177176 A1 | 8/2005 | Gerbi et al. |
| 2005/0203547 A1 | 9/2005 | Weller et al. |
| 2005/0203548 A1 | 9/2005 | Weller et al. |
| 2005/0216036 A1 | 9/2005 | Nakao |

(56) References Cited

U.S. PATENT DOCUMENTS

| | | |
|---|---|---|
| 2005/0216056 A1 | 9/2005 | Valdevit et al. |
| 2005/0222588 A1 | 10/2005 | Vandenbroek et al. |
| 2005/0222590 A1 | 10/2005 | Gadberry et al. |
| 2005/0222665 A1 | 10/2005 | Aranyi |
| 2005/0228411 A1 | 10/2005 | Manzo |
| 2005/0228416 A1 | 10/2005 | Burbank et al. |
| 2005/0234478 A1 | 10/2005 | Wixey et al. |
| 2005/0251183 A1 | 11/2005 | Buckman et al. |
| 2005/0251184 A1 | 11/2005 | Anderson |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277951 A1 | 12/2005 | Smith et al. |
| 2005/0277952 A1 | 12/2005 | Arp et al. |
| 2005/0277953 A1 | 12/2005 | Francese et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2005/0288690 A1 | 12/2005 | Bourque et al. |
| 2006/0004388 A1 | 1/2006 | Whayne et al. |
| 2006/0004390 A1 | 1/2006 | Rosenberg et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020270 A1 | 1/2006 | Jabba et al. |
| 2006/0020271 A1 | 1/2006 | Stewart et al. |
| 2006/0047305 A1 | 3/2006 | Ortiz et al. |
| 2006/0047306 A1 | 3/2006 | Ortiz et al. |
| 2006/0064117 A1 | 3/2006 | Aranyi et al. |
| 2006/0079115 A1 | 4/2006 | Aranyi et al. |
| 2006/0079913 A1 | 4/2006 | Whitfield et al. |
| 2006/0100649 A1 | 5/2006 | Hart |
| 2006/0111731 A1 | 5/2006 | Manzo |
| 2006/0129170 A1 | 6/2006 | Royce et al. |
| 2006/0135992 A1 | 6/2006 | Bettuchi et al. |
| 2006/0163312 A1 | 7/2006 | Viola et al. |
| 2006/0173470 A1 | 8/2006 | Oray et al. |
| 2006/0178683 A1 | 8/2006 | Shimoji et al. |
| 2006/0184182 A1 | 8/2006 | Aranyi et al. |
| 2006/0190013 A1 | 8/2006 | Menn |
| 2006/0195125 A1 | 8/2006 | Sakakine et al. |
| 2006/0200179 A1 | 9/2006 | Barker et al. |
| 2006/0212050 A1 | 9/2006 | D'Agostino et al. |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0259045 A1 | 11/2006 | Damarati |
| 2006/0259049 A1 | 11/2006 | Harada et al. |
| 2006/0264987 A1 | 11/2006 | Sgro |
| 2006/0271072 A1 | 11/2006 | Hummel et al. |
| 2007/0016228 A1 | 1/2007 | Salas |
| 2007/0021761 A1 | 1/2007 | Phillips |
| 2007/0023476 A1 | 2/2007 | Whitman et al. |
| 2007/0023477 A1 | 2/2007 | Whitman et al. |
| 2007/0027458 A1 | 2/2007 | Sixto, Jr. et al. |
| 2007/0034669 A1 | 2/2007 | de la Torre et al. |
| 2007/0038233 A1 | 2/2007 | Martinez et al. |
| 2007/0049947 A1 | 3/2007 | Menn et al. |
| 2007/0049948 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0049953 A2 | 3/2007 | Shimoji et al. |
| 2007/0066981 A1 | 3/2007 | Meagher |
| 2007/0073314 A1 | 3/2007 | Gadberry et al. |
| 2007/0083218 A1 | 4/2007 | Morris |
| 2007/0106314 A1 | 5/2007 | Dunn |
| 2007/0112365 A1 | 5/2007 | Hilal et al. |
| 2007/0118155 A1 | 5/2007 | Goldfarb et al. |
| 2007/0118161 A1 | 5/2007 | Kennedy et al. |
| 2007/0118163 A1 | 5/2007 | Boudreaux et al. |
| 2007/0118174 A1 | 5/2007 | Chu |
| 2007/0123916 A1 | 5/2007 | Maier et al. |
| 2007/0142848 A1 | 6/2007 | Ainsworth et al. |
| 2007/0142851 A1 | 6/2007 | Sixto et al. |
| 2007/0149988 A1 | 6/2007 | Michler et al. |
| 2007/0149989 A1 | 6/2007 | Santilli et al. |
| 2007/0162060 A1 | 7/2007 | Wild |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203509 A1 | 8/2007 | Bettuchi |
| 2007/0203510 A1 | 8/2007 | Bettuchi |
| 2007/0213747 A1 | 9/2007 | Monassevitch et al. |
| 2007/0250080 A1 | 10/2007 | Jones et al. |
| 2007/0265640 A1 | 11/2007 | Kortenbach et al. |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0004636 A1 | 1/2008 | Walberg et al. |
| 2008/0004637 A1 | 1/2008 | Klassen et al. |
| 2008/0004639 A1 | 1/2008 | Huitema et al. |
| 2008/0015615 A1 | 1/2008 | Molitor et al. |
| 2008/0027465 A1 | 1/2008 | Vitali et al. |
| 2008/0027466 A1 | 1/2008 | Vitali et al. |
| 2008/0045981 A1 | 2/2008 | Margolin et al. |
| 2008/0051808 A1 | 2/2008 | Rivera et al. |
| 2008/0065118 A1 | 3/2008 | Damarati |
| 2008/0083813 A1 | 4/2008 | Zemlok et al. |
| 2008/0103510 A1 | 5/2008 | Taylor et al. |
| 2008/0147092 A1 | 6/2008 | Rogge et al. |
| 2008/0147093 A1 | 6/2008 | Roskopf et al. |
| 2008/0154287 A1 | 6/2008 | Rosenberg et al. |
| 2008/0167665 A1 | 7/2008 | Arp et al. |
| 2008/0228199 A1 | 9/2008 | Cropper et al. |
| 2008/0243145 A1 | 10/2008 | Whitfield et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312665 A1 | 12/2008 | Shibata et al. |
| 2008/0319456 A1 | 12/2008 | Hart |
| 2009/0076533 A1 | 3/2009 | Kayan et al. |
| 2009/0088777 A1 | 4/2009 | Miyagi et al. |
| 2009/0088783 A1 | 4/2009 | Kennedy et al. |
| 2009/0171380 A1 | 7/2009 | Whiting |
| 2009/0222003 A1 | 9/2009 | Otley |
| 2009/0228023 A1 | 9/2009 | Cui |
| 2009/0228024 A1 | 9/2009 | Whitfield et al. |
| 2009/0264904 A1 | 10/2009 | Aldrich et al. |
| 2009/0326558 A1 | 12/2009 | Cui et al. |
| 2010/0057105 A1 | 3/2010 | Sorrentino et al. |
| 2010/0057107 A1 | 3/2010 | Sorrentino et al. |
| 2010/0274262 A1 | 10/2010 | Schulz et al. |
| 2010/0274264 A1 | 10/2010 | Schulz et al. |
| 2011/0054498 A1 | 3/2011 | Monassevitch et al. |
| 2011/0087241 A1 | 4/2011 | Nguyen |
| 2011/0087243 A1 | 4/2011 | Nguyen et al. |
| 2011/0112552 A1 | 5/2011 | Lehman et al. |
| 2011/0137323 A1 | 6/2011 | Malkowski et al. |
| 2011/0137324 A1 | 6/2011 | Boudreaux et al. |
| 2011/0144662 A1 | 6/2011 | McLawhorn et al. |
| 2011/0190791 A1 | 8/2011 | Jacobs et al. |
| 2011/0208212 A1 | 8/2011 | Zergiebel et al. |
| 2011/0218553 A1 | 9/2011 | Huitema et al. |
| 2011/0218554 A1 | 9/2011 | Cheng et al. |
| 2011/0218555 A1 | 9/2011 | Huitema |
| 2011/0218556 A1 | 9/2011 | Nguyen et al. |
| 2011/0224696 A1 | 9/2011 | Huitema et al. |
| 2011/0224700 A1 | 9/2011 | Schmidt et al. |
| 2011/0224701 A1 | 9/2011 | Menn |
| 2011/0230900 A1 | 9/2011 | Sarradon |
| 2011/0245847 A1 | 10/2011 | Menn et al. |
| 2011/0245848 A1 | 10/2011 | Rosenberg et al. |

(56) References Cited

U.S. PATENT DOCUMENTS

| | | |
|---|---|---|
| 2011/0295290 A1 | 12/2011 | Whitfield |
| 2011/0313437 A1 | 12/2011 | Yeh |
| 2012/0029534 A1 | 2/2012 | Whitfield et al. |
| 2012/0041455 A1 | 2/2012 | Martinez |
| 2012/0046671 A1 | 2/2012 | Matsuoka et al. |
| 2012/0059394 A1 | 3/2012 | Brenner et al. |
| 2012/0065647 A1 | 3/2012 | Litscher et al. |
| 2012/0109158 A1 | 5/2012 | Zammataro |
| 2012/0116420 A1 | 5/2012 | Sorrentino et al. |
| 2012/0197269 A1 | 8/2012 | Zammataro |
| 2012/0265220 A1 | 10/2012 | Menn |
| 2012/0277765 A1 | 11/2012 | Zammataro et al. |
| 2012/0330326 A1 | 12/2012 | Creston et al. |
| 2013/0110135 A1 | 5/2013 | Whitfield et al. |
| 2013/0131697 A1 | 5/2013 | Hartoumbekis |
| 2013/0165951 A1 | 6/2013 | Blake, III |
| 2013/0165952 A1 | 6/2013 | Whitfield et al. |
| 2013/0172910 A1 | 7/2013 | Malkowski |
| 2013/0172911 A1 | 7/2013 | Rockrohr et al. |
| 2013/0172912 A1 | 7/2013 | Whitfield et al. |
| 2013/0253541 A1 | 9/2013 | Zergiebel |
| 2013/0274767 A1 | 10/2013 | Sorrentino et al. |
| 2013/0289583 A1 | 10/2013 | Zergiebel et al. |
| 2013/0296891 A1 | 11/2013 | Hartoumbekis |
| 2013/0296892 A1 | 11/2013 | Sorrentino et al. |
| 2013/0310849 A1 | 11/2013 | Malkowski |
| 2013/0325040 A1 | 12/2013 | Zammataro |
| 2014/0005693 A1 | 1/2014 | Shelton, IV et al. |
| 2014/0039526 A1 | 2/2014 | Malkowski |
| 2014/0052157 A1 | 2/2014 | Whitfield et al. |
| 2014/0058412 A1 | 2/2014 | Aranyi et al. |
| 2014/0194903 A1 | 7/2014 | Malkowski et al. |
| 2014/0207156 A1 | 7/2014 | Malkowski |
| 2014/0316441 A1 | 10/2014 | Zergiebel et al. |
| 2014/0330291 A1 | 11/2014 | Whitfield et al. |
| 2015/0005790 A1 | 1/2015 | Whitfield et al. |
| 2015/0032131 A1 | 1/2015 | Sorrentino et al. |
| 2015/0066057 A1 | 3/2015 | Rockrohr et al. |
| 2015/0080916 A1 | 3/2015 | Aranyi et al. |
| 2015/0127022 A1 | 5/2015 | Whitfield et al. |

FOREIGN PATENT DOCUMENTS

| | | |
|---|---|---|
| CN | 100571640 C | 12/2009 |
| CN | 101658437 A | 3/2010 |
| CN | 101664329 A | 3/2010 |
| CN | 101664331 A | 3/2010 |
| CN | 201683954 U | 12/2010 |
| CN | 103083059 A | 5/2013 |
| CN | 103181809 A | 7/2013 |
| CN | 103181810 A | 7/2013 |
| CN | 104487006 A | 4/2015 |
| EP | 0 073 655 A1 | 3/1983 |
| EP | 0 086 721 A2 | 8/1983 |
| EP | 0 089 737 A1 | 9/1983 |
| EP | 0 092 300 A1 | 10/1983 |
| EP | 0324166 A2 | 7/1989 |
| EP | 0 392 750 A1 | 10/1990 |
| EP | 0 406 724 A1 | 1/1991 |
| EP | 0 409 569 A1 | 1/1991 |
| EP | 0 569 223 A1 | 11/1993 |
| EP | 0 594 003 A1 | 4/1994 |
| EP | 0 598 529 A2 | 5/1994 |
| EP | 0 622 049 A1 | 11/1994 |
| EP | 0 685 204 A1 | 12/1995 |
| EP | 0 732 078 A2 | 9/1996 |
| EP | 0 755 655 A2 | 1/1997 |
| EP | 0 760 230 A1 | 3/1997 |
| EP | 0 769 274 A1 | 4/1997 |
| EP | 0 769 275 A1 | 4/1997 |
| EP | 0 834 286 A1 | 4/1998 |
| EP | 1 317 906 A1 | 6/2003 |
| EP | 1 609 427 A1 | 12/2005 |
| EP | 1 712 187 A2 | 10/2006 |
| EP | 1 712 191 A2 | 10/2006 |
| EP | 1 757 236 A2 | 2/2007 |
| EP | 1813199 A1 | 8/2007 |
| EP | 1 894 531 A2 | 3/2008 |
| EP | 1 908 423 A2 | 4/2008 |
| EP | 1 913 881 A1 | 4/2008 |
| EP | 1 939 231 A1 | 7/2008 |
| EP | 2 229 895 A1 | 9/2010 |
| EP | 2 332 471 A1 | 6/2011 |
| EP | 2 412 318 A2 | 2/2012 |
| EP | 2 412 319 A2 | 2/2012 |
| EP | 2 752 165 A2 | 7/2014 |
| GB | 1134832 A | 11/1968 |
| GB | 2073022 A | 10/1981 |
| GB | 2 132 899 A | 7/1984 |
| JP | 10-118083 A | 5/1998 |
| JP | 2003-033361 A | 2/2003 |
| JP | 2006-501954 A | 1/2006 |
| JP | 2006-154230 A | 6/2006 |
| JP | 2006-209948 A | 8/2006 |
| JP | 2006-277221 A | 10/2006 |
| JP | 2007-250843 A | 9/2007 |
| JP | 2008-017876 A | 1/2008 |
| JP | 2008-055165 A | 3/2008 |
| JP | 2008-515550 A | 5/2008 |
| JP | 2009-198991 A | 9/2009 |
| WO | 01/65997 A2 | 9/2001 |
| WO | 01-66001 A2 | 9/2001 |
| WO | 01-67965 A1 | 9/2001 |
| WO | 03-086207 A1 | 10/2003 |
| WO | 03-092473 A2 | 11/2003 |
| WO | 2004-032762 A1 | 4/2004 |
| WO | 2005-091457 A1 | 9/2005 |
| WO | 2006-042076 A2 | 4/2006 |
| WO | 2006-042084 A2 | 4/2006 |
| WO | 2006-042110 A2 | 4/2006 |
| WO | 2006-042141 A2 | 4/2006 |
| WO | 2006-135479 A2 | 12/2006 |
| WO | 2008-118928 A2 | 10/2008 |
| WO | 2008-127968 A2 | 10/2008 |

OTHER PUBLICATIONS

International Search Report corresponding to International Application No. PCT-US08-58185, completed Sep. 4, 2008; mailed Sep. 9, 2008; (2 Pages).

International Search Report corresponding to International Application No. PCT-US08-59859, completed Sep. 14, 2008; mailed Sep. 18, 2008; (2 Pages).

Extended European Search Report corresponding to European Application No. EP 07 25 3807.7, completed Nov. 7, 2008; mailed Nov. 26, 2008; (11 Pages).

Extended European Search Report corresponding to European Application No. EP 09 25 2049.3, completed Dec. 11, 2009; mailed Jan. 12, 2010; (3 Pages).

Extended European Search Report corresponding to European Application No. EP 09 25 2050.1, completed Dec. 23, 2009; mailed Jan. 21, 2010; (3 Pages).

Extended European Search Report corresponding to European Application No. EP 09 25 2051.9, completed Dec. 21, 2009; mailed Jan. 28, 2010; (3 Pages).

Extended European Search Report corresponding to European Application No. EP 09 25 2052.7, completed Nov. 16, 2009; mailed Nov. 24, 2009; (3 Pages).

Extended European Search Report corresponding to European Application No. EP 09 25 2053.5, completed Nov. 24, 2009; mailed Dec. 1, 2009; (3 Pages).

Extended European Search Report corresponding to European Application No. EP 09 25 2054.3, completed Jan. 7, 2010; mailed Jan. 22, 2010; (3 Pages).

Extended European Search Report corresponding to European Application No. EP 09 25 2056.8, completed Jan. 8, 2010; mailed Feb. 5, 2010; (3 Pages).

Extended European Search Report corresponding to European Application No. EP 10 25 0497.4, completed May 4, 2010; mailed May 12, 2010; (6 Pages).

(56) References Cited

OTHER PUBLICATIONS

Extended European Search Report corresponding to European Application No. EP 10 25 2079.8, completed Mar. 8, 2011; mailed Mar. 17, 2011; (3 Pages).
European Search Report corresponding to European Application No. EP 05 81 0218.7, completed Apr. 18, 2011; mailed May 20, 2011; (3 pages).
European Search Report corresponding to European Application No. EP 05 80 7612.6, completed May 2, 2011; mailed May 20, 2011; (3 pages).
Extended European Search Report corresponding to European Application No. EP 10 25 1737.2, completed May 9, 2011; mailed May 20, 2011; (4 pages).
Extended European Search Report corresponding to European Application No. EP 11 25 0214.1, completed May 25, 2011; mailed Jun. 1, 2011; (3 Pages).
Extended European Search Report corresponding to European Application No. EP 11 00 2681.2, completed May 31, 2011; mailed Jun. 10, 2011; (3 Pages).
European Search Report corresponding to European Application No. EP 05 80 2686.5, completed Jan. 9, 2012; mailed Jan. 18, 2012; (3 Pages).
Extended European Search Report corresponding to European Application No. EP 12 15 1313.9, completed Mar. 20, 2012 and mailed Apr. 12, 2012; (5 Pages).
Extended European Search Report corresponding to European Application No. EP 12 16 1291.5, completed Apr. 24, 2012 and mailed May 4, 2012; (5 Pages).
Extended European Search Report corresponding to European Application No. EP 12 16 5891.8, completed Jun. 12, 2012 and mailed Jun. 20, 2012; (6 Pages).
Extended European Search Report corresponding to European Application No. EP 12 16 2288.0, completed Jun. 4, 2012 and mailed Jul. 7, 2012; (6 Pages).
Extended European Search Report corresponding to European Application No. EP 12 16 4955.2, completed Aug. 23, 2012 and mailed Sep. 4, 2012; (5 Pages).
Extended European Search Report corresponding to European Application No. EP 11 25 0754.6, completed Oct. 22, 2012 and mailed Oct. 31, 2012; (6 Pages).
Extended European Search Report corresponding to European Application No. EP 12 18 6401.1, completed Nov. 22, 2012 and mailed Nov. 30, 2012; (7 Pages).
Extended European Search Report corresponding to European Application No. EP 12 18 6448.2, completed Nov. 28, 2012 and mailed Dec. 10, 2012; (6 Pages).
Extended European Search Report corresponding to European Application No. EP 12 19 1706.6, completed Dec. 19, 2012 and mailed Jan. 8, 2013; (6 Pages).
Extended European Search Report corresponding to EP 12 19 8745.7, completed Mar. 19, 2013 and mailed Apr. 11, 2013; (8 Pages).
Extended European Search Report corresponding to EP 12 15 2989.5, completed Apr. 9, 2013 and mailed Apr. 18, 2013; (9 Pages).
Extended European Search Report corresponding to EP 08 73 2820.9, completed Jul. 2, 2013 and mailed Jul. 9, 2013; (10 Pages).
Extended European Search Report corresponding to EP 13 17 2008.8, completed Aug. 14, 2013 and mailed Aug. 28, 2013; (8 Pages).
Extended European Search Report corresponding to EP 13 16 6382.5, completed Nov. 19, 2013 and mailed Nov. 28, 2013; (8 Pages).
Extended European Search Report corresponding to EP 11 25 0194.5, completed Nov. 25, 2013 and mailed Dec. 3, 2013; (8 Pages).
Extended European Search Report corresponding to EP 10 25 1798.4, completed Dec. 12, 2013 and mailed Jan. 2, 2014; (9 Pages).
"Salute II Disposable Fixation Device", Technique Guide—Laparoscopic and Open Inguinal and Ventral Hernia Repair; Davol, A Bard Company, 2006; (7 Pages).
Extended European Search Report corresponding to EP 10 25 2112.7, completed Jul. 29, 2014 and mailed Aug. 5, 2014; (8 pp).
Extended European Search Report corresponding to EP 14 15 1673.2, completed Apr. 25, 2014 and mailed May 8, 2014; (8 pp).
Australian Examination Report corresponding to AU 2011211463 dated Apr. 13, 2015; 3 pages.
Japanese Office Action corresponding to JP 2011-160130 mailed Dec. 1, 2014.
Chinese Office Action corresponding to CN 201210015011.8 issued Jan. 4, 2015.
Japanese Office Action corresponding to JP 2011-160126 mailed Jan. 9, 2015.
Japanese Office Action corresponding to JP 2011-184521 mailed Jan. 15, 2015.
Extended European Search Report corresponding to 14 18 2236.1 dated Jan. 20, 2015.
Chinese Office Action corresponding to CN 201110201736.1 issued Feb. 9, 2015.
Extended European Search Report corresponding to EP 14 16 1540.1 dated Feb. 27, 2015.
Australian Office Action corresponding to AU 2010226985 issued Mar. 31, 2015.
Australian Office Action corresponding to AU 2013211526 issued Apr. 6, 2015.
Australian Office Action corresponding to AU 2011211463 issued Apr. 13, 2015.
Australian Office Action corresponding to AU 2013254887 issued Apr. 14, 2015.
Japanese Office Action corresponding to JP 2013-225272 mailed May 1, 2015.
European Office Action corresponding to EP 12 152 989.5 dated May 4, 2015.
Australian Office Action corresponding to AU 2009212759 issued May 7, 2015.
Japanese Office Action corresponding to JP 2013-229070 mailed May 8, 2015.
Japanese Office Action corresponding to JP 2013-229996 mailed May 8, 2015.
European office action received from corresponding EP 11250754.6 dated Jul. 22, 2015.
Chinese First Office Action corresponding to counterpart Int'l Appln. No. CN 201210586826.1 dated Dec. 30, 2015.
Extended European Search Report corresponding to counterpart Int'l Appln. No. EP 15 19 1313.4 dated Feb. 1, 2016.
Extended European Search Report corresponding to counterpart Int'l Appln. No. EP 15 18 5362.9 dated Feb. 12, 2016.
Extended European Search Report corresponding to counterpart Int'l Appln. No. EP 12 19 7813.4 dated Mar. 7, 2016.
Canadian Office Action corresponding to counterpart Int'l Appln. No. CA 2,676,465 dated Mar. 8, 2016.
Japanese Office Action corresponding to counterpart Int'l Appln. No. JP 2014-245081 dated Mar. 18, 2016.
Japanese Office Action corresponding to counterpart Int'l Appln. No. JP 2015-005629 dated Mar. 18, 2016.
Extended European Search Report corresponding to counterpart Int'l Appln. No. EP 15 19 3549.1 dated Mar. 22, 2016.
International Search Report and Written Opinion corresponding to counterpart Int'l Appln. No. PCT/CN2015/082199 dated Mar. 31, 2016.
Extended European Search Report corresponding to counterpart Int'l Appln. No. EP 15 19 7251.0 dated Apr. 8, 2016.
Extended European Search Report corresponding to counterpart Int'l Appln. No. EP 16 15 0739.7 dated May 17, 2016.
Canadian Office Action corresponding to counterpart Int'l Appln. No. CA 2,716,672 dated May 31, 2016.
Canadian Office Action corresponding to counterpart Int'l Appln. No. CA 2,717,448 dated May 31, 2016.
Canadian Office Action corresponding to counterpart Int'l Appln. No. CA 2,721,951 dated Jun. 1, 2016.
Partial European Search Report corresponding to counterpart Int'l Appln. No. EP 16 15 0287.7 dated Jun. 16, 2016.
Chinese Second Office Action corresponding to counterpart Int'l Appln. No. CN 201210555570.8 dated Jun. 20, 2016.

(56) References Cited

OTHER PUBLICATIONS

International Search Report & Written Opinion corresponding to Int'l Appln. No. PCT/CN2015/091603 dated Jul. 8, 2016.
Chinese Office Action issued in corresponding application No. 201510419902.3 on Jan. 4, 2017.

\* cited by examiner

SELF-CENTERING CLIP AND JAW

CROSS-REFERENCE TO RELATED APPLICATION

The present application is a Divisional application which claims the benefit of and priority to U.S. patent application Ser. No. 13/196,109 entitled "Self-Centering Clip and Jaw" filed on Aug. 2, 2011, now U.S. Pat. No. 9,011,464, which claims priority to, and benefit of, U.S. Provisional Patent Application No. 61/409,131 entitled "Self-Centering Clip and Jaw" filed on Nov. 2, 2010, the entire contents of each of which are hereby incorporated by reference herein.

BACKGROUND

Technical Field

The present disclosure relates to surgical instruments. More particularly, the present disclosure relates to an endoscopic surgical clip applier and corresponding surgical clips.

Description of Related Art

Endoscopic staplers and clip appliers are known in the art and are used for a number of distinct and useful surgical procedures. In the case of a laparoscopic surgical procedure, access to the interior of an abdomen is achieved through narrow tubes or cannulas inserted through a small entrance incision in the skin. Minimally invasive procedures performed elsewhere in the body are often generally referred to as endoscopic procedures. Typically, a tube or cannula device is extended into the patient's body through the entrance incision to provide an access port. The port allows the surgeon to insert a number of different surgical instruments therethrough using a trocar and for performing surgical procedures far removed from the incision.

During a majority of these procedures, the surgeon must often terminate the flow of blood or another fluid through one or more vessels. The surgeon will often apply a surgical clip to a blood vessel or another duct to prevent the flow of body fluids therethrough during the procedure. An endoscopic clip applier is known in the art for applying a single clip or a series of clips during a surgical procedure. Such clips are typically fabricated from a biocompatible material and are usually compressed over a vessel. Once applied to the vessel, the compressed clip terminates the flow of fluid therethrough.

Endoscopic clip appliers that are able to apply multiple clips in endoscopic or laparoscopic procedures during a single entry into the body cavity are described in commonly-assigned U.S. Pat. Nos. 5,084,057 and 5,100,420 to Green et al., which are both incorporated by reference in their entirety. Another multiple endoscopic clip applier is disclosed in commonly-assigned U.S. Pat. No. 5,607,436 by Pratt et al., the contents of which is also hereby incorporated by reference herein in its entirety. These devices are typically, though not necessarily, used during a single surgical procedure. U.S. patent application Ser. No. 08/515,341 now U.S. Pat. No. 5,695,502 to Pier et al., the disclosure of which is hereby incorporated by reference herein, discloses a resterilizable surgical clip applier. The clip applier advances and forms multiple clips during a single insertion into the body cavity. This resterilizable clip applier is configured to receive and cooperate with an interchangeable clip magazine so as to advance and form multiple clips during a single entry into a body cavity.

One significant design goal in the manufacture of clip appliers is to align the surgical clips between the jaws and maintain the alignment of the legs of the clip throughout a formation of the clip onto the body tissue or vessel. It is therefore desirable to provide a surgical clip and surgical clip applier that promote proper alignment of the legs of the clip within the jaws thereof and throughout the formation of the clip onto the body tissue or vessel.

SUMMARY

In accordance with the present disclosure, an apparatus for application of surgical clips to body tissue is provided. The apparatus includes a handle assembly having a handle and a trigger moveable with respect to the handle. An elongated shaft extends distally from the handle assembly and includes one or more surgical clips disposed therein. Each surgical clip includes a pair of legs connected to each other at one end by a crossbar. Each of the pair of legs has an inwardly facing surface and an outwardly facing surface. The outwardly facing surface of each leg has a raised profile protruding therefrom and extending longitudinally therealong. A jaw assembly is disposed at a distal end of the elongated shaft and includes first and second opposed jaws moveable between a spaced apart position and an approximated position. Each of the jaws defines a recess extending longitudinally along opposing inner surfaces thereof. Each of the recesses defines a longitudinally extending groove having a profile substantially complementary to the raised profile of the legs of the one or more surgical clips. The legs of each of the surgical clips are positionable at least partially within respective grooves of the recesses of the jaws.

In one embodiment, the outwardly facing surfaces of the legs of each surgical clip have a substantially triangular transverse cross-sectional profile. The groove defined in each recess of the jaws may also have a substantially triangular transverse cross-sectional profile.

In yet another embodiment, each leg of each surgical clip has a chevron transverse cross-sectional profile. The cross bar of each surgical clip may also have a chevron shaped transverse cross-sectional profile.

In still another embodiment, each groove of each jaw is defined by a first wall and a second wall angled toward each other and defining an angle therebetween. Similarly, the outwardly facing surface of each leg of each surgical clip may be defined by a first wall and a second wall angled toward each other and defining an angle therebetween. Further, the angle defined by the first wall and the second wall of the outer surface of each leg of each surgical clip may be smaller than the angle defined by the first wall and the second wall of the groove of the jaws.

In still yet another embodiment, a shoulder is defined at an interface between the recess and the groove of each jaw at opposed sides of the groove.

In accordance with another embodiment of the present disclosure, a jaw assembly for use in a surgical clip applier configured to apply surgical clips to body tissue is provided. Each of the surgical clips includes a pair of opposed legs, each having an outwardly projecting longitudinally extending raised profile. The jaw assembly includes first and second opposed jaws moveable between a spaced apart position and an approximated position. Each of the jaws defines a recess extending longitudinally along opposing inner surfaces thereof. Each of the recesses defines a longitudinally extending groove and each of the jaws is configured for positioning of a leg of a surgical clip at least partially within the recess of the jaw and for receiving the raised portion of each leg of the surgical clip in a groove of a respective jaw.

In one embodiment, the jaw assembly includes a shoulder defined at an interface between the recess and the groove of each jaw at opposed sides of the groove. Further, the groove defined in the recess of each jaw may have a substantially triangular transverse cross-sectional profile or a chevron transverse cross-sectional profile.

In accordance with another embodiment of the present disclosure, each surgical clip includes a pair of legs connected to each other at one end by a crossbar. Each leg includes an inwardly facing surface and an outwardly facing surface. The outwardly facing surface of each leg includes a plurality of spaced-apart protrusions formed thereon, each protrusion defining a raised profile protruding from the outwardly facing surface of the leg thereof. This surgical clip may be used in conjunction with any of the jaw assemblies described above.

BRIEF DESCRIPTION OF THE DRAWINGS

Various embodiments of the subject instrument are described herein with reference to the drawings wherein.

DETAILED DESCRIPTION

Figure 1:
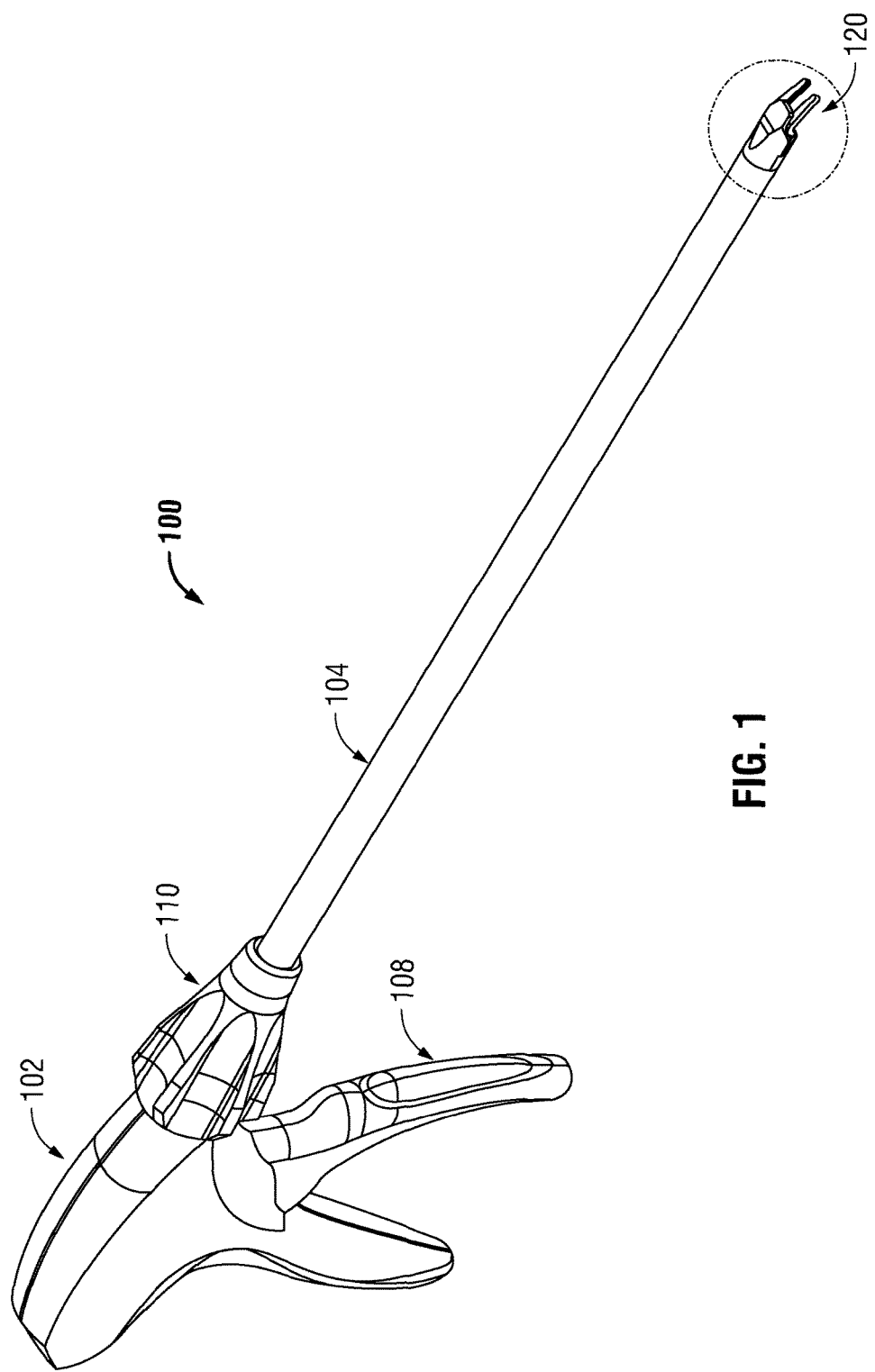
FIG. 1 is a perspective view of a surgical clip applier.

Embodiments of a surgical clip applier in accordance with the present disclosure will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Figure 2:
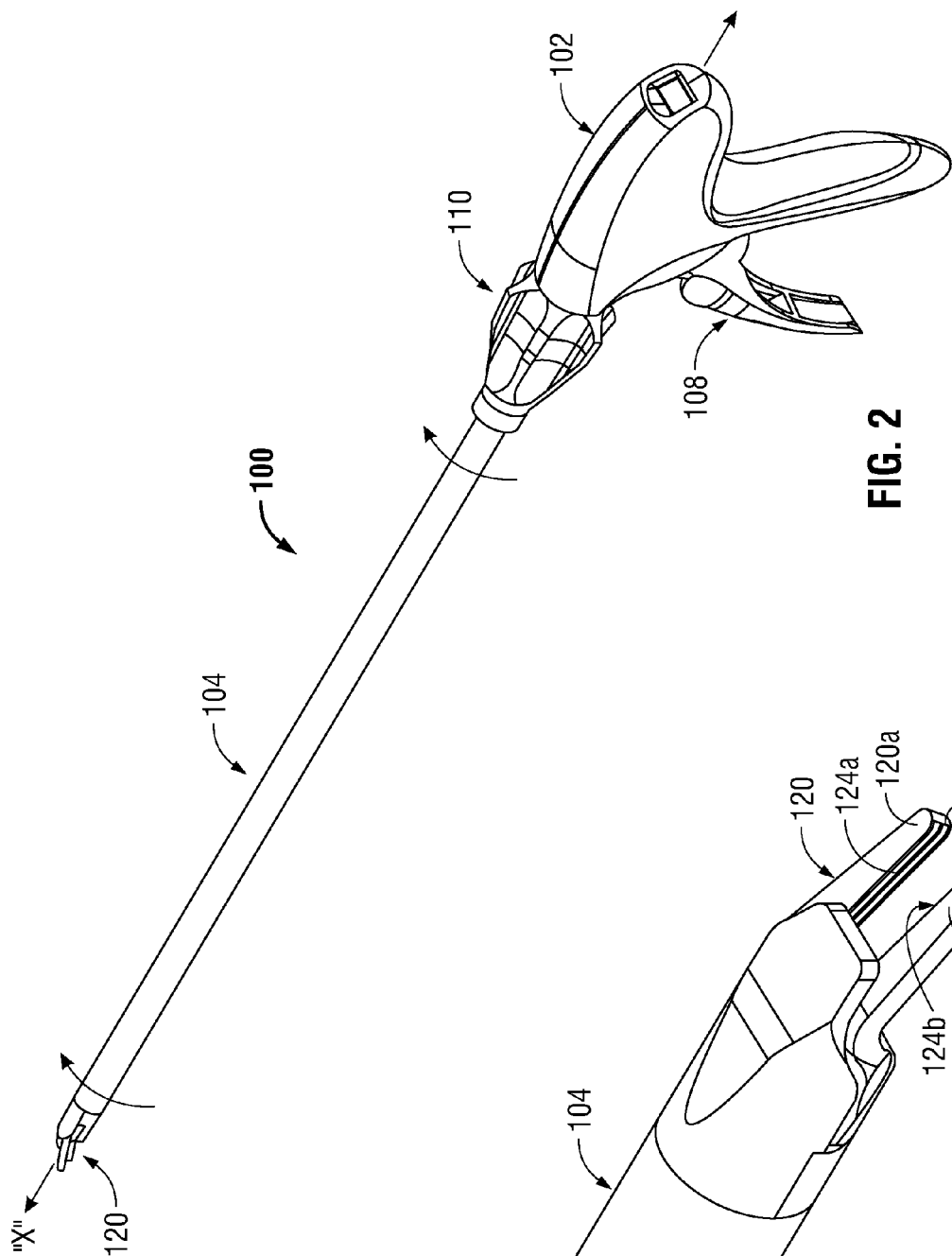
FIG. 2 is a further perspective view of the surgical clip applier of FIG. 1, illustrating a rotation of an elongate tubular member thereof.
Figure 3:
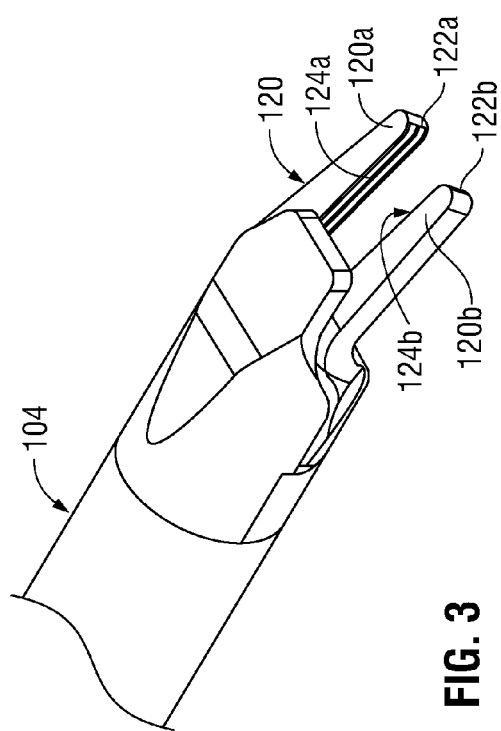
FIG. 3 is an enlarged, perspective view of the jaw structure of the surgical clip applier of FIGS. 1 and 2.

Referring briefly to FIGS. 1-3, a surgical clip applier in accordance with the present disclosure is generally designated as 100. Surgical clip applier 100 generally includes a handle assembly 102 and an endoscopic portion including a shaft assembly 104 extending distally from handle assembly 102 and having a jaw assembly 120 disposed at a distal end thereof. A stack of surgical clips is typically loaded and/or retained within shaft assembly 104 in a manner so as to slide therewithin and/or therealong. A complete description of the inner-workings and operation of surgical clip applier 100 can be found in commonly-assigned U.S. patent application Ser. No. 12/055,446 to Whitfield et. al., the entire contents of which are hereby incorporated by reference herein.

With continued reference to FIGS. 1-3, jaw assembly 120 is mounted in the distal end of shaft assembly 104 such that jaws 120a, 120b are longitudinally stationary relative thereto. A knob 110 may be rotatably mounted on a distal end of handle assembly 102 and affixed to shaft assembly 104 to transmit and/or provide 360° rotation to shaft assembly 104 and jaws 120a, 120b about a longitudinal axis "x" thereof. As will be described in greater detail hereinbelow, jaws 120a and 120b of jaw assembly 120 each define a recess 122a, 122b within an inwardly facing surface thereof as well as a groove 124a, 124b defined within the respective recesses 122a, 122b. The recesses 122a and 122b and the grooves 124a and 124b are configured for guiding passage of a surgical clip (see FIGS. 6-10) therethrough.

Figure 4:
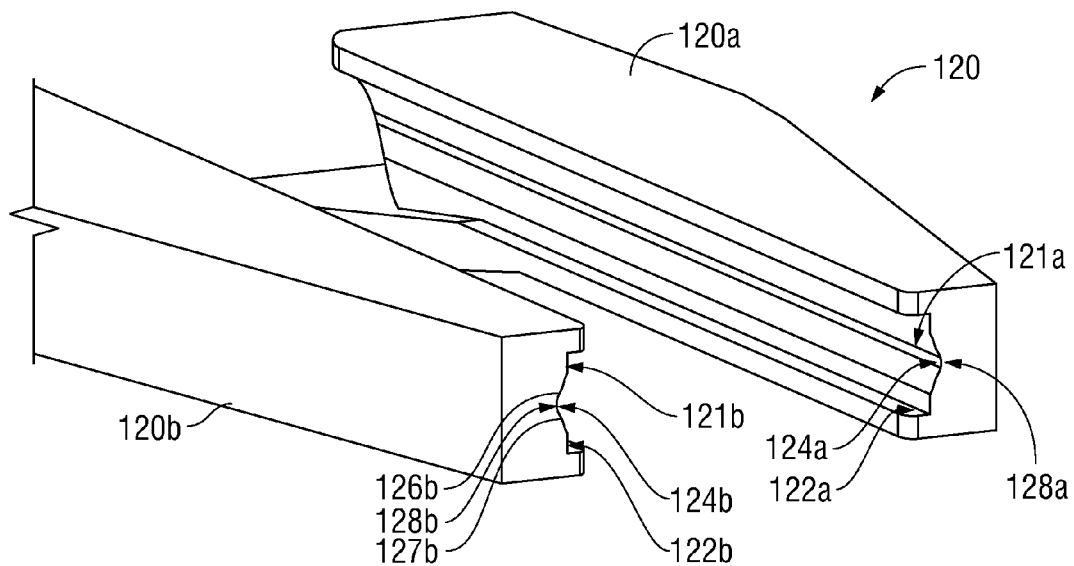
FIG. 4 is a front, perspective view of a jaw assembly for use in the surgical clip applier of FIG. 1.
Figure 5:
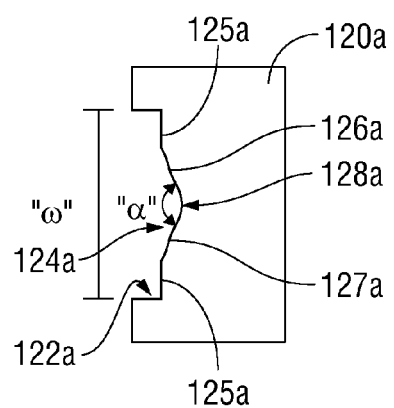
FIG. 5 is a distal end view of one of the jaws of the jaw assembly of FIG. 4.
Figure 6:
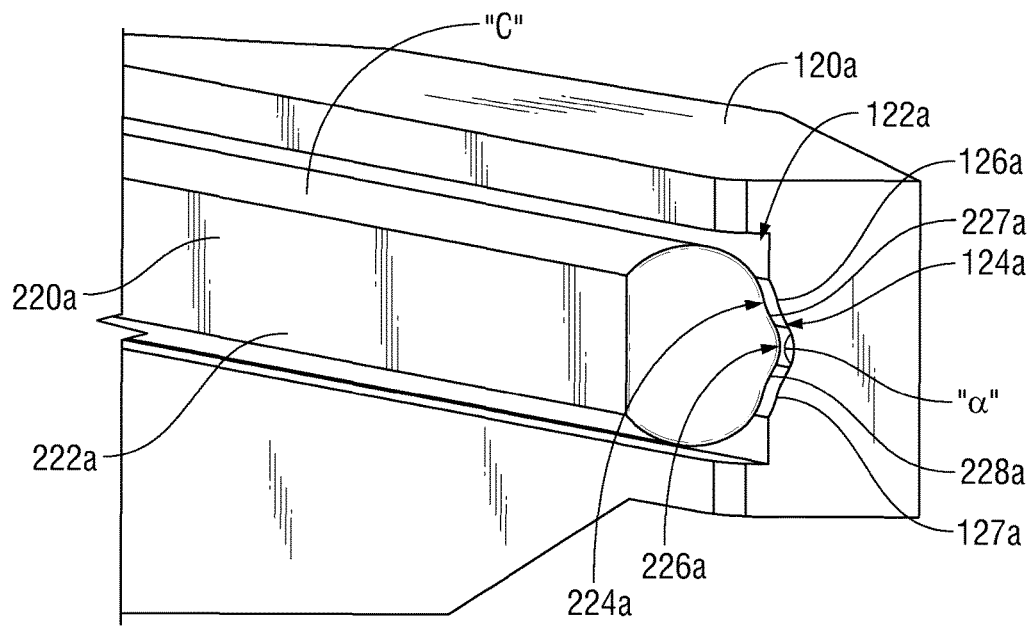
FIG. 6 is a front, perspective view of the jaw of FIG. 5 shown having a portion of a surgical clip supported therein.

Referring now to FIGS. 4-6, jaws 120a, 120b are shown each having a respective recess 122a, 122b extending longitudinally therealong. More specifically, recesses 122a and 122b are defined within inwardly facing surfaces 121a and 121b of jaws 120a and 120b, respectively. Recesses 122a and 122b each define a width "w" (FIG. 5) and may have a generally rectangular transverse cross-sectional profile. As can be appreciated, width "w" is sufficiently large to allow passage therethrough of a clip "C" (FIG. 6). In other words, the width "w" is larger than a diameter "d" of clip "C" (FIG. 8) such that clip "C" is positionable at least partially within and slidable through recesses 122a and 122b of jaws 120a and 120b, respectively. Recesses 122a, 122b may be formed within jaws 120a, 120b, respectively, via machining, or any other suitable process.

With continued reference to FIGS. 4-6, grooves 124a and 124b are defined within recesses 122a and 122b of jaws 120a and 120b, respectively. Similar to recesses 122a and 122b, grooves 124a and 124b extend longitudinally along jaw members 120a and 120b, respectively. The width "w" of recess 122a of jaw 120a is larger than a maximum diameter of groove 124a such that a pair of shoulders 125a is defined at the interfaces between recess 122a groove 124a. Similarly to jaw 120a, the width of recess 122b of jaw 120b is larger than a maximum diameter of groove 124b such that a pair of shoulders is defined at the interfaces between recess 122b groove 124b.

Grooves 124a and 124b are defined by first walls 126a, 127a and second walls 126b, 127b, respectively. Each pair of walls 126a, 127a and 126b, 127b extend toward each other at an angle "α," eventually converging to a nadir 128a and 128b of grooves 124a and 124b, respectively. Thus, grooves 124a and 124b define a substantially triangular, or V-shaped transverse cross-sectional profile, as best shown in FIGS. 4-6. It is also envisioned that first and second walls 126a, 126b and 127a, 127b may be non-linear, e.g., curved or bowed, as shown in FIGS. 5-6, to thereby define a chevron transverse cross-sectional profile. Additionally, grooves 124a, 124b and/or recesses 122a, 122b may be centered with respect to a height of jaws 120a and 120b, respectively, or with respect to width "w" of recesses 122a, 122b. Further, grooves 124a and 124b may be centered with respect to recesses 120a and 120b defined within jaws 120a and 120b, respectively.

Figure 7:
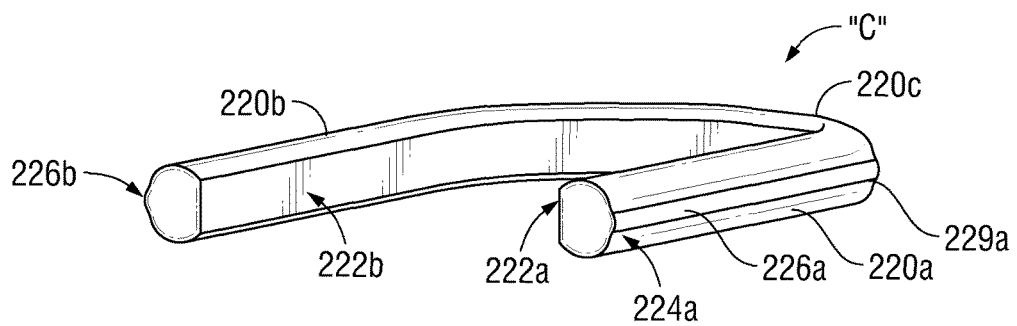
FIG. 7 is a front, perspective view of a surgical clip for use in the surgical clip applier of FIG. 1.
Figure 8:
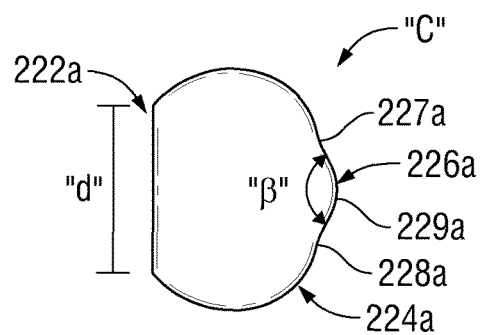
FIG. 8 is a transverse, cross-sectional view of one leg of the surgical clip of FIG. 7.
Figure 9:
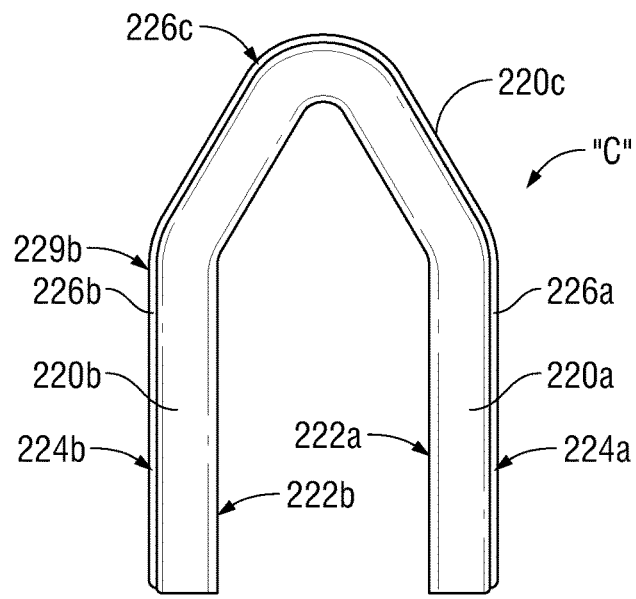
FIG. 9 is a top, plan view of the surgical clip of FIG. 7.

Referring now to FIGS. 7-9, each clip "C" includes a pair of legs 220a, 220b interconnected by a crown, backspan, or crossbar 220c. An inwardly facing surface 222a, 222b of each leg 220a and 220b, respectively, defines a generally flat geometry such that upon forming of clip "C" about a body tissue or vessel, inwardly facing surfaces 222a and 222b of legs 220a and 220b consistently and evenly clamp around the body tissue or vessel. Outwardly facing surfaces 224a and 224b of legs 220a and 220b, respectively, may define a generally circular transverse cross-sectional profile and may include raised profiles 226a and 226b protruding from respective outwardly facing surfaces 224a and 224b and extending longitudinally therealong. Crossbar 220c may similarly include a raised profile 226c protruding therefrom and interconnecting raised profile 226a of leg 220a with raised profile 226b of leg 220b to form an uninterrupted raised profile substantially along the entire outwardly facing surface of clip "C."

More particularly, as seen in FIG. 8, raised profile 226a is defined by first and second walls 227a and 228a, respectively, extending outwardly from outwardly facing surface 224a of leg 220a. First and second walls 227a and 228a, respectively, are angled toward each other at an angle "β" to a peak 229a to define a substantially triangular, V-shaped or chevron transverse cross-sectional profile. Similarly to leg 220a, raised profile 226b of leg 220b is defined by first and second walls extending outwardly from an outwardly facing surface of leg 220b. The first and second walls are also angled toward each other at an angle "β," to a peak.

It is envisioned that angle "β," the angle defined by walls 227a and 228a of raised profile 226a, and similarly defined by the first and second walls of raised profile 226b, is about equal to or less than the angle "α" defined between the first and second walls 126a, 126b and 127a, 127b of grooves 124a and 124b of jaws 120a and 120b, respectively, such that raised profile 226a is at least partially positionable within groove 124a of jaw 120a and such that raised profile 226b is at least partially positionable within groove 124b of jaw 120b.

Further, it is envisioned that first and second walls 227a and 228a of leg 220a and the first and second walls of leg 220b be non-linear, e.g., curved or bowed. Additionally, the non-linear shape of the first and second walls of legs 220a, 220b may be shaped similarly to non-linear walls 126a, 127a and 126b, 127b of grooves 124a and 124b of jaws 120a and 120b, respectively. Accordingly, where angle "α" is equal to angle "β," raised profiles 226a and 226b are thus shaped complementary to grooves 124a and 124b, respectively. However, it is also contemplated that where angles "α" and "β" are different, e.g., where "α" is greater than "β," raised profiles 226a and 226b are shaped substantially, or quasi-complementarily to grooves 124a and 124b, respectively.

Figure 8A:
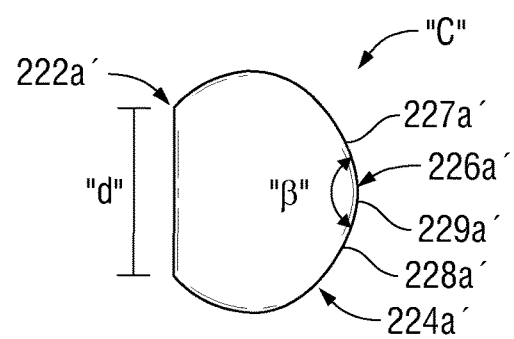
FIG. 8A is a transverse, cross-sectional view of one leg of a surgical clip according to another embodiment of the present disclosure.

Turning now to FIG. 8A, an outer profile for an alternate clip "C1" is illustrated. As seen in FIG. 8A, an outwardly facing surface 224a' of a leg 220a' of clip "C1" includes substantially planar first and second walls 227a' and 228a' that are angled toward each other, by and angle "β", to a peak 229a' to define a substantially triangular shaped, V-shaped or chevron shaped transverse cross-sectional profile 226a'.

Figure 8B:
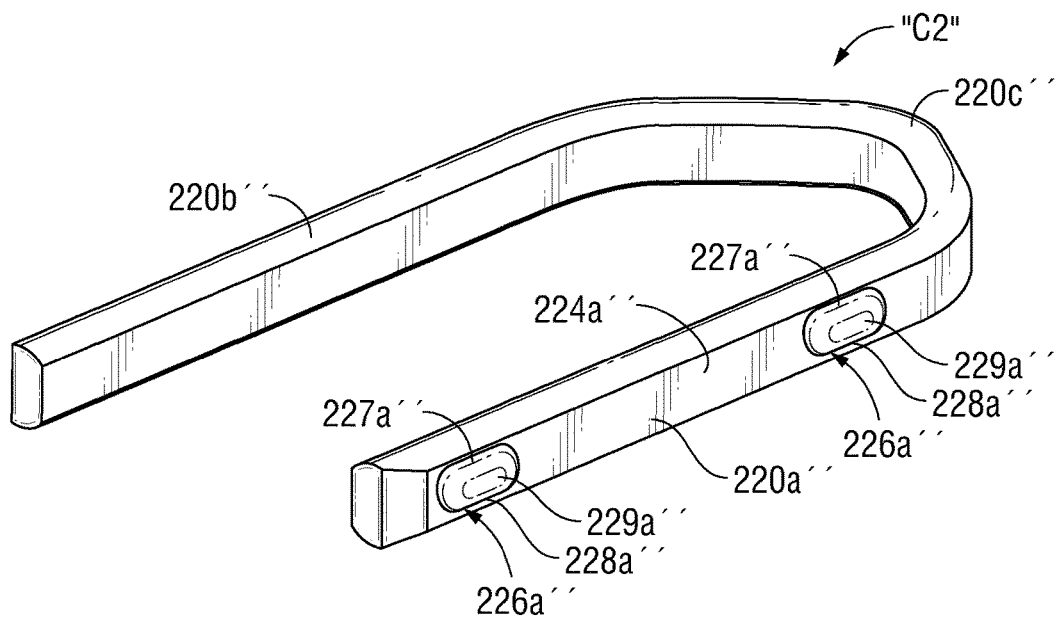
FIG. 8B is a front, perspective view of another embodiment of a surgical clip according to the present disclosure.

Referring to FIG. 8B, another embodiment of a clip "C2" configured for use with surgical clip applier 100 (FIGS. 1-3) includes a pair of legs 220a", 220b" interconnected by a crossbar 220c". Clip "C2" is similar to clip "C" (FIGS. 7, 8 and 9) and may include any of the features associated with clip "C" described above. However, different from clip "C" (FIGS. 7, 9 and 9), clip "C2" includes a plurality of discrete, spaced-apart, raised protrusions 226a" protruding from outwardly facing surface 224a" of leg 220a". Clip "C2" may also include protrusions (not explicitly shown) extending similarly from the outwardly facing surface of leg 220b" and/or from the outwardly facing surface of crossbar 220c". The protrusions, e.g., protrusions 226a", may be formed via coining, or any other suitable manufacturing process.

With continued reference to FIG. 8B, each protrusion 226a" includes a pair of opposed angled surfaces 227a", 228a" that are angled toward each other, defining an angle "β" (see FIG. 8) therebetween, and ultimately converging to define a peak 229a". In other words, angled surfaces 227a", 228a" and peak 229a" cooperate to define a substantially triangular, V-shaped or chevron transverse cross-sectional profile. Further, although two protrusions 226a" are shown, it is envisioned that greater or fewer that two protrusions 226a" be provided and/or that protrusions 226a" be spaced further-apart or closer-together relative to one another. Clip "C2" may otherwise be configured similarly to clip "C" (FIGS. 7, 8 and 9) or clip "C1" (FIG. 8A), discussed above.

The operation of surgical clip applier 100, to crimp or form a surgical clip "C" around a target body tissue, such as, for example, a vessel (FIG. 10), will now be described with reference to FIGS. 1-10.

Initially, clip applier 100 is positioned such that a tissue or a vessel "V" to be clamped is disposed between jaws 120a and 120b. As trigger 108 is squeezed or actuated, trigger 108 causes clip "C" to translate distally into recesses 122a and 122b of jaws 120a and 120b, respectively, such that at least a portion of leg 220a is positioned within recess 122a of jaw member 120a and such that at least a portion of leg 220b is positioned within recess 122b of jaw member 120b. Thus, legs 220a and 220b of clip "C," similar to jaws 120a and 120b, are now also positioned surrounding tissue or vessel "V" to be clamped.

In this position, the raised profiles 226a and 226b protruding from legs 220a and 220b, respectively, are positioned within grooves 124a and 124b of jaws 120a and 120b, respectively. This configuration ensures proper alignment of legs 220a and 220b of clip "C" relative to one another and, in turn, clip "C" within jaws 120a, 120b, respectively. In other words, recesses 122a and 122b, in cooperation with grooves 124a and 124b serve as a "track" to permit longitudinal translation of legs 220a and 220b of clip "C" therethrough, but substantially inhibit rotational, vertical and/or transverse movement and/or canting of legs 220a and 220b of clip "C" relative to one another, thereby helping to ensure proper alignment of clip "C" within jaws 120.

Figure 10:
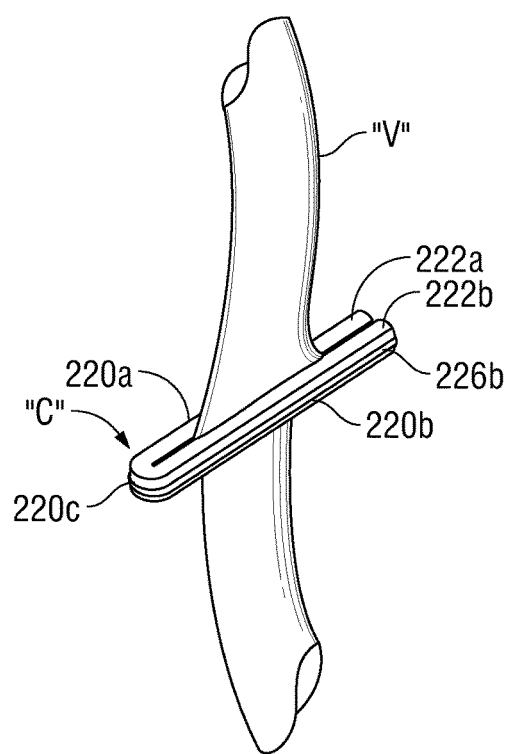
FIG. 10 is a perspective view of the surgical clip of FIG. 7 formed on a vessel.

At this point, legs 220a and 220b of clip "C" are positioned within recesses 122a, 122b, with raised profiles 226a and 226b positioned within grooves 124a, 124b of jaws 120a, 120b, respectively. As shown in FIGS. 7-9, clip "C" initially defines an unformed configuration in which legs 220a and 220b are spaced apart relative to one another. As trigger 108 is squeezed further, jaws 120a and 120b are moved from the open position toward the approximated position, thereby beginning to form surgical clip "C" interposed therebetween. As seen in FIG. 10, surgical clip "C" may be formed or crimped onto a vessel "V" or any other biological tissue. During formation of clip "C," the flat, inwardly facing surfaces 222a and 222b of legs 220a and 220b, are approximated toward each other to thereby effect clamping of vessel "V." Alternatively, inwardly facing surfaces 222a, 222b may include one or more features to promote a secure and effective clamp about tissue or vessel "V."

During formation of clip "C," the complementary shaped raised profiles 226a and 226b of legs 220a and 220b of clip "C" are retained within grooves 124a and 124b of jaws 10a, 120b and, more specifically, legs 220a and 220b of clip "C" are retained with recesses 122a and 122b of jaws 120a, 120b, such that rotational, vertical and/or transverse movement of clip "C" relative to jaw assembly 120 is substantially inhibited. Accordingly, as jaws 120a and 120b are moved together to form clip "C," legs 220a and 220b are similarly brought together, in a substantially aligned coplanar orientation, to clamp about vessel "V." In other words, the recesses 122 and grooves 124 of the jaws 120a, 120b and corresponding configuration of clip "C", including raised profiles 226 thereof, reduce incidents and/or prevent scissoring of legs 220a and 220 during formation of clip "C." Increasing incidents of proper alignment of legs 220a and 220b helps in the proper formation of clips "C."

Once clip "C" has been clamped about vessel "V," as shown in FIG. 10, trigger 108 may be released, allowing jaw assembly 120 to return back to the spaced apart position. The above-described operation of surgical clip applier 100 may then be repeated for subsequent clamping of clips "C" about tissue.

In accordance with the present disclosure, in an embodiment, by providing grooves 124a, 124b in the jaws that interact and cooperate with raised profiles 226c of the clips, the width "w" of recesses 122a and 122b may be sufficiently large, relative to a maximum width of the legs of the clip, to accommodate variations in manufacturing tolerances with respect to a width dimension of the legs of the clips, with respect to a linearity of the legs of the clips, with respect to a width dimension of the recesses of the jaws, and with regard to a linearity of the recesses of the jaws.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. An apparatus for application of surgical clips to body tissue, the apparatus comprising:
   a handle assembly having a handle and a trigger moveable with respect to the handle;
   an elongated shaft extending distally from the handle assembly, the elongated shaft including at least one surgical clip disposed therein, each surgical clip including a pair of legs connected to each other at one end by a crossbar, each of the pair of legs having an inwardly facing surface, an outwardly facing surface, and defining a length, the outwardly facing surface including a plurality of spaced-apart protrusions formed thereon and extending the length thereof, each protrusion defining a raised profile protruding from the outwardly facing surface of the leg, wherein each of the plurality of protrusions is defined by at least one wall; and
   a jaw assembly disposed at a distal end of the elongated shaft, the jaw assembly including first and second opposed jaws moveable between a spaced apart position and an approximated position, each of the jaws defining a recess extending longitudinally along opposing inner surfaces thereof, each of the recesses defining a longitudinally extending groove having a profile substantially complementary to the raised profile of the protrusions of the legs of the at least one surgical clip, wherein the groove of each jaw is defined by at least one wall;
   wherein the at least one surgical clip is configured to longitudinally slide from the elongated shaft into the jaw assembly such that the legs of the at least one surgical clip are positioned at least partially within and slid along respective grooves of the recesses of the jaws and such that the plurality of spaced-apart protrusions of each leg are positioned at least partially within the groove of the recess of the respective jaw and slid therealong with the least one wall of each of the plurality of protrusions sliding along the at least one wall of the groove of the recess of the respective jaw.

2. The apparatus according to claim 1, wherein the protrusions each have a substantially triangular transverse cross-sectional profile.

3. The apparatus according to claim 1, wherein the groove defined in each recess of the jaws has a substantially triangular transverse cross-sectional profile.

4. The apparatus according to claim 1, wherein each protrusion has a chevron transverse cross-sectional profile.

5. The apparatus according to claim 1, wherein the groove of each jaw is defined by a first wall and a second wall angled toward each other and defining an angle therebetween.

6. The apparatus according to claim 5, wherein each protrusion is defined by a first wall and a second wall angled toward each other and defining an angle therebetween.

7. The apparatus according to claim 6, wherein the angle defined by the first wall and the second wall of each protrusion is smaller than the angle defined by the first wall and the second wall of the groove of each jaw.

8. The apparatus according to claim 1, wherein a shoulder is defined at an interface between the recess and the groove of each jaw at opposed sides of the groove.

9. The apparatus according to claim 1, wherein the plurality of spaced-apart protrusions of each leg of each surgical clip includes a first protrusion adjacent a free end of the respective leg and a second protrusion adjacent the crossbar of the respective surgical clip.

10. The apparatus according to claim 9, wherein the first protrusion of each leg is positionable at least partially within the groove of the recess of the respective jaw towards a distal end thereof, and wherein the second protrusion of each leg is positionable at least partially within the groove of the recess of the respective jaw towards a proximal end thereof.

11. An apparatus for application of surgical clips to body tissue, the apparatus comprising:
   a jaw assembly including first and second opposed jaws moveable between a spaced apart position and an approximated position, each of the jaws defining a recess extending longitudinally along opposing inner surfaces thereof, each of the recesses defining a longitudinally extending groove, wherein each groove of each jaw is defined by a first wall and a second wall angled toward each other and defining an angle therebetween; and
   at least one surgical clip, each surgical clip including a pair of legs connected to each other at one end by a crossbar, each of the pair of legs having an inwardly facing surface and an outwardly facing surface, the outwardly facing surface including a plurality of spaced-apart protrusions formed thereon, each protrusion defining a raised profile protruding from the outwardly facing surface of the leg, wherein each protrusion is defined by first and second longitudinally-extending walls angled toward each other and defining an angle therebetween, wherein the angle defined by the walls of each protrusion is smaller than the angle defined by the walls of the groove of each jaw, wherein the at least one surgical clip is longitudinally slidable relative to the jaw assembly such that the legs of the at least one surgical clip are slid at least partially within respective grooves of the recesses of the jaws and such that the plurality of spaced-apart protrusions of each leg are positioned at least partially within the groove of the recess of the respective jaw and slid therealong with the first and second walls of each of the plurality of spaced-apart protrusions of each leg sliding along the respective first and second walls of the groove of the recess of the respective jaw.

12. The apparatus according to claim 11, wherein the protrusions each have a substantially triangular transverse cross-sectional profile.

13. The apparatus according to claim 11, wherein the groove defined in each recess of the jaws has a substantially triangular transverse cross-sectional profile.

14. The apparatus according to claim 11, wherein each protrusion has a chevron transverse cross-sectional profile.

15. The apparatus according to claim 11, wherein a shoulder is defined at an interface between the recess and the groove of each jaw at opposed sides of the groove.

16. The apparatus according to claim 11, further including:
a handle assembly having a handle and a trigger moveable with respect to the handle; and
an elongated shaft extending distally from the handle assembly, the elongated shaft including the at least one surgical clip disposed therein, wherein the jaw assembly is disposed at a distal end of the elongated shaft.

17. The apparatus according to claim 11, wherein the plurality of spaced-apart protrusions of each leg of each surgical clip includes a first protrusion adjacent a free end of the respective leg and a second protrusion adjacent the crossbar of the respective surgical clip.

18. The apparatus according to claim 17, wherein the first protrusion of each leg is positionable at least partially within the groove of the recess of the respective jaw towards a distal end thereof, and wherein the second protrusion of each leg is positionable at least partially within the groove of the recess of the respective jaw towards a proximal end thereof.

* * * * *